(12) United States Patent
Suzuki et al.

(10) Patent No.: US 6,814,239 B2
(45) Date of Patent: Nov. 9, 2004

(54) HIGH-PURITY STANDARD PARTICLE PRODUCTION APPARATUS, METHOD AND PARTICLES

(75) Inventors: Nobuyasu Suzuki, Kanagawa (JP); Takehito Yoshida, Kanagawa (JP); Toshiharu Makino, Kanagawa (JP); Yuka Yamada, Kanagawa (JP)

(73) Assignee: Matsushita Electric Industrial Co., LTD, Osaka (JP)

( * ) Notice: Subject to any disclaimer, the term of this patent is extended or adjusted under 35 U.S.C. 154(b) by 22 days.

(21) Appl. No.: 10/076,070

(22) Filed: Feb. 15, 2002

(65) Prior Publication Data

US 2002/0139250 A1 Oct. 3, 2002

(30) Foreign Application Priority Data

Feb. 14, 2001 (JP) .......................... 2001-037736

(51) Int. Cl.[7] .............................................. B07B 1/00
(52) U.S. Cl. ........................................................ 209/11
(58) Field of Search ............................ 209/3, 133, 135, 209/10, 11, 12.2, 127.1, 127.2, 129, 131; 96/16

(56) References Cited

U.S. PATENT DOCUMENTS

| | | | | |
|---|---|---|---|---|
| 4,534,034 A | * | 8/1985 | Hohla et al. | 372/59 |
| 4,574,004 A | * | 3/1986 | Schmidt-Ott et al. | 95/79 |
| 4,987,007 A | * | 1/1991 | Wagal et al. | 427/526 |
| 6,282,222 B1 | * | 8/2001 | Wieser et al. | 372/74 |
| 6,454,862 B1 | * | 9/2002 | Yoshida et al. | 118/722 |
| 6,527,865 B1 | * | 3/2003 | Sajoto et al. | 118/715 |

FOREIGN PATENT DOCUMENTS

| | | | |
|---|---|---|---|
| JP | 07-283098 | | 10/1995 |
| JP | 2000-146818 | * | 5/2000 |
| JP | 2000-279893 A | * | 10/2000 |
| JP | 2000-282222 A | * | 10/2000 |
| JP | 1 139 438 A2 | * | 4/2001 |
| JP | 2001-133387 A | * | 5/2001 |

* cited by examiner

*Primary Examiner*—Donald P. Walsh
*Assistant Examiner*—Joseph C Rodriguez
(74) *Attorney, Agent, or Firm*—Browdy and Neimark, P.L.L.C.

(57) ABSTRACT

An apparatus for producing high-purity standard particles produces nanometer-sized high-purity standard particles of monodispersive uniform structure efficiently, with the abatement of contamination and damage. The apparatus includes a particle generation chamber, a particle classification chamber and a particle collecting chamber. The particle generation chamber excites a semiconductor target with pulse laser beam under a low-pressure rare gas ambient so as to detach and eject materials from the target into the ambient gas, in which those materials are condensed and grow into high-purity particles. The particle classification chamber subjects the high-purity particles as generated to classification, and the particles collecting chamber collects high-purity standard particles as classified onto a substrate.

12 Claims, 6 Drawing Sheets

HIGH-PURITY STANDARD PARTICLE PRODUCTION APPARATUS, METHOD AND PARTICLES

BACKGROUND OF THE INVENTION

1. Field of the Invention

The present invention relates to a high-purity standard particles production apparatus and the same particles, especially, pertaining to a nanometer-sized standard particles production technique that is indispensable for verifying a particle counter that is used for controlling nanometer-sized high-purity particles and for measuring the collecting efficiency of a filter that is used for removing nanometer-sized impurity particles contained in the gas phase where a semiconductor or a liquid crystal is produced as well as to a production technique of nanometer-sized monodisperse high-purity standard particles that is prospective of various functional occurrences caused by quantum size effect.

2. Description of Prior Art

In the recent semiconductor industry, a pattern size in the nanometer scale of 0.13 $\mu$m is to be soon realized while that of 0.18 $\mu$m is in mass production. In accordance with the tendency to minify the pattern size, it requires that the remaining dusts present in the production process thereof that affect the yield of the production output be thoroughly controlled. Especially, not only nanometer-sized impurity particles containing such chemical components as heavy metal, carbon and so forth are in themselves capable of causing such inconveniences as the disconnection of a semiconductor device or the short-circuit thereof, but also contamination caused by the impurities dispersed during the heating treatment of the production process thereof gives significant affect on the quality control thereof, which should be held under thorough control.

On the other hand, observing nanometer-sized particles apart from the contamination thereof by impurities, the particle of 10 nm or below happens to show property or function that is not observed in the bulk state thereof. For instance, when such IV group elements as silicon (Si) and germanium (Ge), which elements are hard to emit light in the bulk state thereof because they are indirect transition semiconductors, turn to become the particles of several nanometers in size, it is known that those particles emit strong visible light in a room temperature. However, because the nanometer particle has large proportion of surface exposure atoms, which proportion amounts to 40% in the scale of 5 nm, it is extremely sensitive to the contamination of impurities and the occurrence of crystal defects so that it has been generally accepted that such particle is hard to be developed into a high-performance function device. Further, as the novel property and function of the particle as mentioned above is brought by a so-called quantum size effect or in accordance with the size thereof, it is required to put the size of the respective particles in order so as to obtain monodispersive particles for the purpose of enhancing such a novel function thereof as monochromatic light ejection and so forth.

Such nanometer-sized particles production methods as a colloidal method and an in-gas evaporation method are conventionally known. The colloidal method is arranged such that metallic salt is reduced in alcohol along with a polymer surface-active agent under reflux condition so as to generate metallic particles coated with the polymer compound in a colloidal state, which method belongs to a low-temperature synthetic method and is said to be easier to control the diameter of the particles so as to obtain the same in an uniform size in comparison with another similar methods. Then, such vapor-phase growth methods as the above in-gas evaporation method by means of arc discharge and resistance heating are arranged such that not only metal but also evaporable compound are evaporated and cooled in an inert gas so as to be formed into particles.

The nanometer-sized particles producible by the colloidal method are limited to the materials that are soluble in alcohol, and the particles as produced by the same method are coated with a polymer compound, the selectivity of which materials is an issue to be solved yet. Then, when the raw material of a high fusing point is an object for the above vapor-phase growth method or the in-gas evaporation method by means of arc discharge or resistance heating as mentioned above, the heating portion of the reaction chamber occupies a comparatively large space thereof and the possibility that the raw material reacts with a vaporizing pot can not be disregarded, so that it is hard to obtain high-purity particles keeping the stoichiometric composition of the raw material intact. In addition, the geometric standard deviation of the particle diameter distribution is comparatively large, so that it is difficult to put to use the particles as produced for monodispersive standard particles.

As mentioned above, in view of the prior art, a much cleaner and trouble-free production process is sought after in order to obtain high-purity standard particles of nm size in scale,

SUMMARY OF THE INVENTION

In view of the inconveniences encountered with the prior art, the present invention is to provide a high-purity standard particles production apparatus that allows nanometer-sized high-purity standard particles of monodispersive uniform structure, the material for which particles is wide in selection to be produced in an efficient manner with the abatement of contamination or damage thereon and the same particles.

The high-purity standard particles production apparatus according to the present invention comprises a particle generation chamber where high-purity particles are generated by laser ablation in an ambient gas, a particle classification chamber where high-purity standard particles of a diameter as required are classified from high-purity particles as generated in the particle generation chamber and a particle collecting chamber where high-purity standard particles as classified are collected.

This apparatus allows nanometer-sized high-purity standard particles of wide selectivity in material and monodispersive uniform structure to be produced and collected in an efficient manner with the abatement of contamination and damage thereon.

The present invention having the above characteristics is embodied in an apparatus comprising a particles generation chamber where high-purity particles are generated in an ambient gas by laser ablation, a particles classification chamber where high-purity standard particles of a diameter as required are classified from the high-purity particles generated in the generation chamber and a particles collecting chamber where the high-purity standard particles as classified are collected. This apparatus allows nanometer-sized high-purity standard particles of monodispersive uniform structure to be produced and collected in an efficient manner with the abatement of contamination and damage thereon.

Then, the particle classification chamber of the high-purity standard particles production apparatus according to the present invention is characterized in being provided with the plurality of particle classification means, which means make the distribution width of the diameter of the standard particles narrower.

Further, heating treatment by means of infrared radiation is performed on the high-purity standard particles at the downstream of the classification chamber of the apparatus according to the present invention, which makes spherical the high-purity standard particles having various shapes through cohesion and improves the crystallization thereof.

Then, the high-purity standard particles production apparatus according to the present invention is characterized in being provided with a gas refining means to substantially remove the impurities contained in a raw material gas supplied as an ambient gas, which restrains the impurities contained in such ambient gas as oxygen and the contamination of the particles as generated so as to highly purify the standard particles as produced.

Moreover, the particle collecting chamber of the high-purity standard particles production apparatus according to the present invention is characterized in being provided with an orifice that reduces the cross section of a piping system through the passage of the high-purity standard particles, which enlarges the difference in pressure between the upstream and downstream locations with regard to the orifice so as to improve the ejecting speed of the standard particles from the orifice and to augment the mobility of the standard particles as ejected from the orifice while to allow the particles to be deposited with concentration, with the result that the collecting efficiency of the nanometer-sized standard particles improves.

Then, the present invention realizes nanometer-sized high-purity standard particles as produced by the above production apparatus, which particles are provided with monodispersive uniform structure, irrespective of the kinds of material in use.

As described above, a high-purity standard particles production apparatus together with the same standard particles as produced is provided herein, which apparatus allows nanometer-sized high-purity standard particles of wide selectivity in material and monodispersive uniform structure to be produced in an efficient manner with the abatement of the contamination and damage thereof.

The means to solve the prior issue and the advantages brought thereby according to the present invention are described below in more details with reference to the accompanying drawings.

DETAILED DESCRIPTION OF THE PREFERRED EMBODIMENTS

Figure 1:
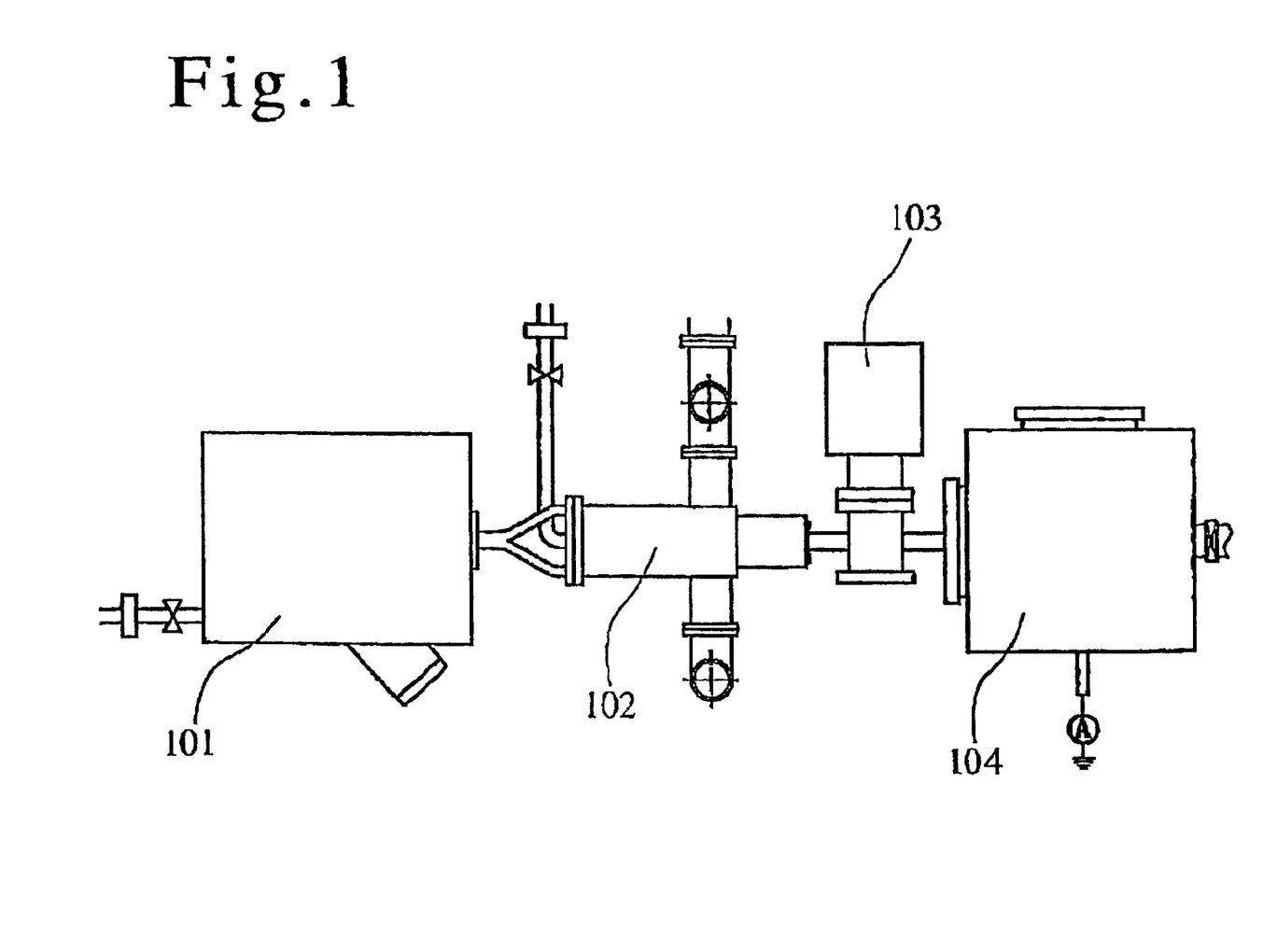
FIG. 1 is the whole structural view of a high-purity standard particles production apparatus to show one example of the preferred embodiment of the present invention.

Hereinafter, the preferred embodiment of a high-purity standard particles production apparatus according to the present invention is described in details with reference to FIGS. 1 through 6. FIG. 1 shows one example of the whole structure of the high-purity standard particles production apparatus according to the preferred embodiment of the present invention, which apparatus comprises a particles generation chamber 101 to generate fine particles, a particles classification chamber 102 to classify the fine particle as generated according to the diameter thereof, a standard particles heating section 103 to heat the fine particles as classified and a particles collecting chamber 104 to collect the high-purity standard particles as heated.

Figure 2:
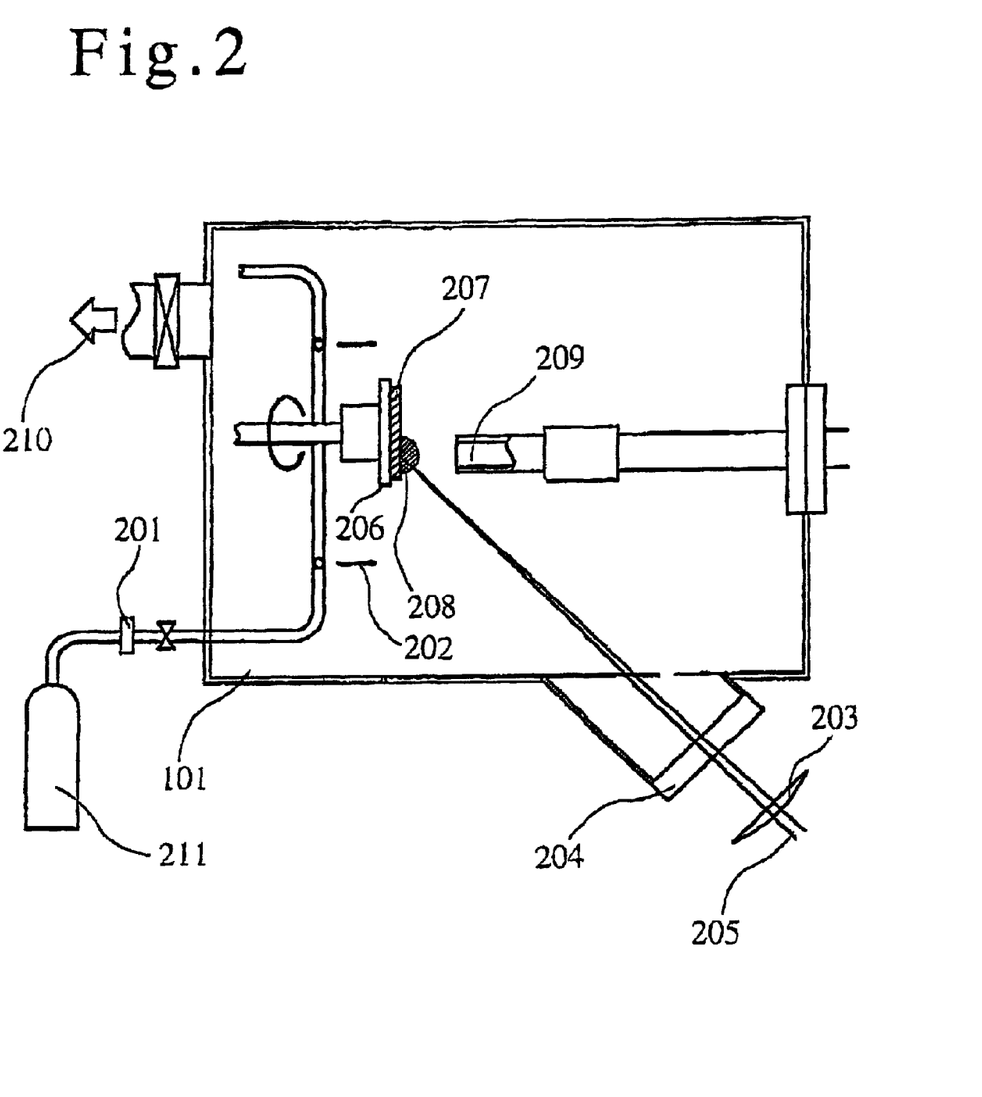
FIG. 2 is a sectional view of a particles generation chamber to show one example of the preferred embodiment of the present invention.

Here, the basic structure of the particles generation chamber 101 is shown in FIG. 2. FIG. 2 is a sectional view of the generation chamber 101 to show the basic structure thereof. As shown in the drawing, the particles generation chamber 101 comprises a gas introduction system to introduce a carrier gas 202, e.g. a Helium gas with the purity of 99.9999% into a high-purity particles generation chamber 101 through a gas ejection outlet disposed in ring shape at the constant mass flow rate of Qa, e.g. at the rate of 1.0 l/min via a gas refining means 211 and a mass flow controller 201, a target 207, e.g. the target made from tantalum (Ta) with the purity of 99.5% and the diameter of 50 mm and the thickness of 5 mm that is fixed on a target holder 206 provided with a rotational mechanism, which target is excited by a pulse laser beam 205, e.g. Q-switch Nd:YAG laser to generate the secondary higher harmonic with the wavelength of 532 nm, the pulse width of 7 ns and the pulse energy of 0.5 J, which laser beam is condensed at a condenser 203 disposed at the angle of 45 degrees with regard to the carriage course of the high-purity particles and is introduced into a particles generation chamber 101 through a laser beam introduction window 204, a particles intake pipe 209 disposed in the same growth direction as the carriage course of the high-purity particles of an ablation plume 208 that is excited with the energy density of 177 J/cm$^2$ by the pulse laser beam 205 and a super-high vacuum exacuation system 210 essentially consisting of a turbopump that evacuates the particles generation chamber 101 prior to the production of the high-purity particles so as to put the chamber 101 under the super-high vacuum condition of lower than $1\times10^{-9}$ Torr. According to this arrangement, the high-purity particles are generated by laser ablation in an ambient gas.

Figure 3:
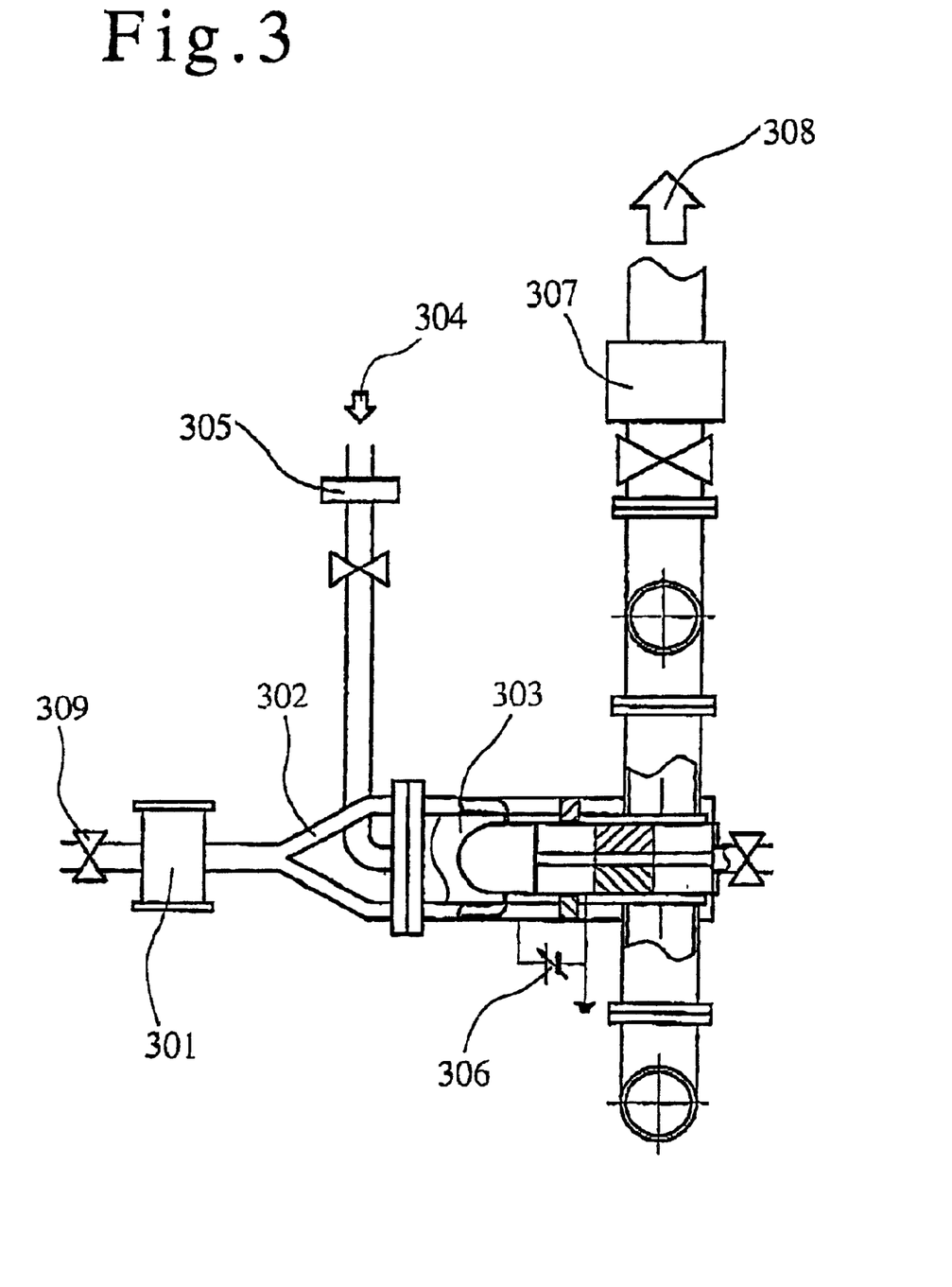
FIG. 3 is a partly sectional view of a particles classification chamber to show one example of the preferred embodiment of the present invention.

Then, the basic structure of the particles classification chamber 102 is shown in FIG. 3. FIG. 3 is a partly sectional side view of the classification chamber 102 to show the basic structure thereof. As shown in the drawing, the particles classification chamber 102 comprises a charge chamber 301 to charge univalent by use of a radioactive isotope, e.g. americium (Am), the high-purity particles generated at the particles generation chamber 101 and carried at the mass flow rate of Qa, a particles inflow pipe 302 that is disposed linearly from the particles generation chamber 101 towards the particles collecting chamber 104, which pipe is equidistantly separated into four divisions, for instance, a differential mobility analyzer 303 of a double cylindrical structure into which the charged high-purity particles are flowed from the particles inflow pipe 302 and that classifies the particles into the diameters as required, a mass flow controller 305 to introduce a sheath gas 304, e.g. a Helium gas with the purity of 99.9999%, which gas is intended for causing a flow at the constant mass flow rate of Qc, e.g. at the rate of 5.0 l/min inside the differential mobility analyzer 303, into the same analyzer 303, a direct current power source 306 to form an electrostatic field between the double cylinders thereof and a sheath gas evacuate system 308 to evacuate the sheath gas at the constant mass flow rate of Qc by means of a helical pump and as such through a high conductance evacuate pipe, which gas is controlled by a mass flow meter 307 disposed upstream to the pump. This arrangement allows the high-purity particles generated at the particles generation chamber 101 to be classified into the diameters as required.

Here, the high-purity particles may be charged by such vacuum ultraviolet light source as $Ar_2$ excimer lamp with the wavelength of 126 nm or be charged by both a radioactive isotope and a vacuum ultraviolet light source.

In addition, it is arranged that only one differential mobility analyzer is exemplified, a series of which analyzers may be disposed for further narrowing the distribution width of the particles diameters.

Further, the impurities contained in the sheath gas may be removed by 0.5 ppb or below so as to abate the contamination of the particles by setting up a gas refining means to the upstream of the mass flow controller 305.

Figure 4:
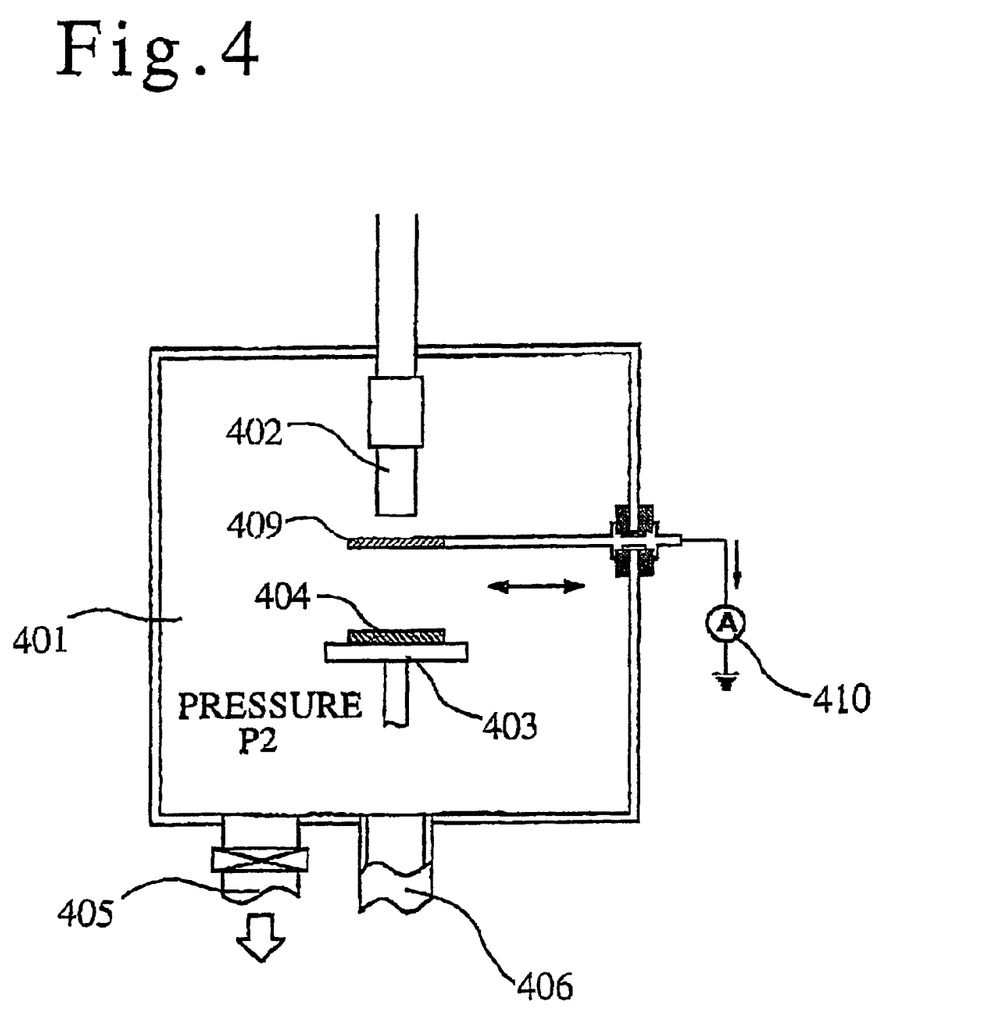
FIG. 4 is a sectional view of a particles collecting chamber to show one example of the preferred embodiment of the present invention.
Figure 5:
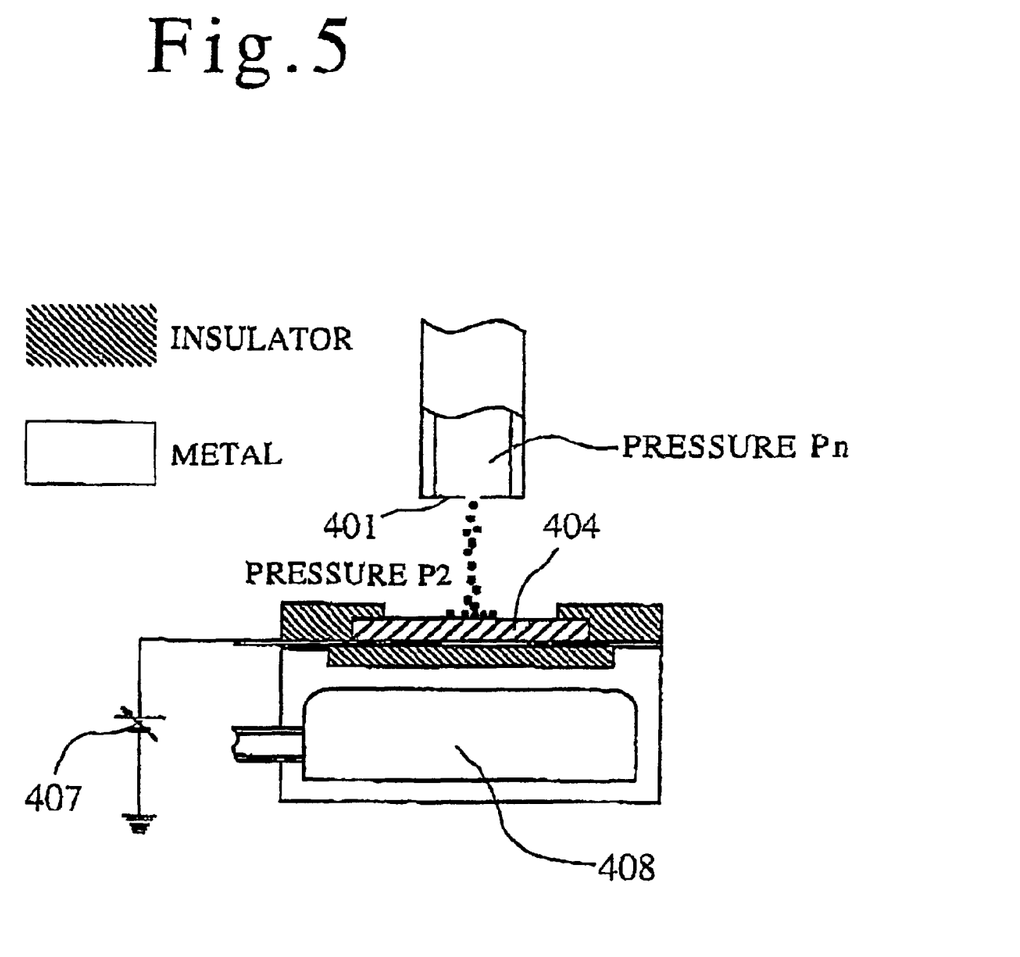
FIG. 5 is a sectional view of a particles collecting chamber to show the neiborhood of the substrate thereof, which is one example of the preferred embodiment of the present invention.

Moreover, the basic structure of the particles collecting chamber 104 is shown in FIGS. 4 and 5. FIG. 4 is a sectional view of the collecting chamber 104 to show the basic structure thereof while FIG. 5 is a sectional view to show the arrangement thereof in the neiborhood of its substrate. As shown in the drawings, the particles collecting chamber 104 comprises a nozzle 402, into which the carrier gas containing the high-purity standard particles as classified into the sole diameter at the particles classification chamber 102 through the generation chamber 101 is flowed and from an orifice 401 of which with the diameter of e.g. 4 mm the gas is emitted, which orifice is provided at the tip end of the nozzle, a collecting substrate 404 to collect the high-purity particles, which substrate is fixed onto a substrate holder 403, a super-high vacuum evacuation system 405 essentially consisting of a turbopump that evacuates the collecting chamber 104 prior to the production of the high-purity standard particles to put the same chamber into the super-high vacuum condition of lower than $1 \times 10^{-9}$ Torr, a gas evacuation system 406 essentially consisting of a helical pump to perform the differential evacuation of the carrier gas such that the particles generation chamber 101 is kept under the constant pressure of e.g. 10 Torr, a fine current measuring terminal 409 to collect the high-purity particles charged univalent so as to measure the concentration of the particles as collected as a current and an ammeter 410 to display the fine current as measured, wherein the high-purity standard particles are collected onto the substrate 404.

Here, the production of the high-purity standard particles of the sole diameter and uniform structure is described below with reference to FIGS. 2 through 6. First, prior to the production thereof, in order to prevent the particles from being contaminated and damaged, a valve 309 as shown in FIG. 3 is closed and the particles generation chamber 101 is evacuated by the super-high vacuum evacuation system 210 as shown in FIG. 2, which system essentially consists of a turbopump so as to put the same chamber into the super-high vacuum condition of lower than $1 \times 10^{-9}$ Torr, after which the system 210 is closed.

At the same time, the particles classification chamber 102 and the particles collecting chamber 104 are evacuated by the super-high vacuum evacuation system 405 essentially consisting of a turbopump as shown in FIG. 4 so as to put the same chamber into the super-high vacuum condition of lower than $1 \times 10^{-9}$ Torr, after which the system 405 is closed.

Then, the carrier gas 202, the concentration of the impurities of which gas is lowered by 0.5 ppb or below through the gas refining means 211, is introduced into the particles generation chamber 101 at the mass flow rate of Qa or 0.5 l/min in this embodiment by means of the mass flow controller 201 as shown in FIG. 2.

Then, the valves 310 and 311 are opened, and the gas evacuation system 406 essentially consisting of a helical pump is controlled on the basis of the pressure applied in the particles generation chamber 101, which pump performs the differential evacuation of the carrier gas, so as to keep the chamber 101 at the constant pressure of P1, e.g. 10 Torr.

Here, the surface of the target 207 is excited by the pulse laser beam 205 that is condensed as shown in FIG. 2 so as to cause ablation reaction thereon, which allows natural oxide formed on the surface thereof and such impurities as metallic or carbon compounds attached thereon to be completely removed, after which the system 406 is closed. At this moment, the oscillation of the pulse laser beam 205 comes to a halt.

As described above, the removal of the natural oxide formed on the surface of the target 207 and the impurities attached thereon prevents them from being mixed into the high-purity particles in production stage.

Then, the adjustment of the mass flow controller 201 permits the carrier gas 202, the concentration of the impurities of which gas is lowered by 0.5 ppb or below through the gas refining means 211, to be introduced into the particles generation chamber 101 at the constant mass flow rate of Qa or at the rate of 1.0 l/min under normal condition.

At the same time, the sheath gas 304 or a high-purity rare gas, e.g. a Helium gas with the purity of 99.9999% is introduced into the differential mobility analyzer 303 at the mass flow rate of 5.0 l/min under normal condition by means of the mass flow controller 305 as shown in FIG. 3.

Here, the gas evacuation system 406 essentially consisting of a helical pump is opened for the differential evacuation of the carrier gas such that the inside of the high-purity particles generation chamber 101 is kept under the constant pressure of P1, e.g. 10 Torr.

Simultaneously, the sheath gas evacuation system 308 essentially consisting of a helical pump provided in the particles classification chamber 102 is opened, and the system 308 is controlled on the basis of the indication value of the mass flow meter 307 so that the value becomes 5.0 l/min so as to evacuate the sheath gas at the constant mass flow rate of Qc.

The pressure loss of a conductance variable valve provided in the orifice 401 and the gas evacuation system 406 allows the inside of the particles collecting chamber 104 to be kept under the constant pressure of P2, e.g. 1.0 Torr.

The sheath and carrier gases evacuation as mentioned above permits the internal pressure P1 of the generation chamber 101, that P2 of the collecting chamber and the mass flow rate Qc of the evacuated sheath gas to be precisely controlled.

Further, the alteration of the aperture in diameter of the orifice 401 to 2 mm allows the difference between the internal pressures Pn of the nozzle 402 and P2 to enlarge such that the Pn amounts to 7.4 Torr while the P2 amounts to 0.1 Torr.

Then, the introduction of the pulse laser beam 205 into the particles generation chamber 101 follows the oscillation thereof. At this moment, the materials excited by the pulse laser beam 205 so as to be desorbed and ejected from the target 207 under ablation reaction dissipate away their kinetic energy to the molecules of the ambient gas so as to promote the aerial condensation and growth thereof, with the result that they grow into several tens to decimal nanometer-sized high-purity particles.

After the particles generation chamber is evacuated under super-high vacuum condition as described above, the high-purity gas, the concentration of the impurities in which gas is lowered by 0.5 ppb or below, is introduced into the generation chamber and kept at the constant pressure of P1 under precise control, which allows nanometer-sized particles to cohere and grow while keeping their high purity intact.

Then, the local excitation with higher energy by the pulse laser beam of short pulse width permits even such high melting point metal as tantalum (Ta) with the fusing point of 2172 degrees Centigrade and such materials as palladium (Pd) and platinum (Pt) that are prone to form an alloy with an evaporating pot made from e.g. tungsten (W) by means of an ordinary evaporating method to be generated into nanometer-sized high-purity particles by laser ablation within the ambient gas.

Subsequently, the high-purity particles generated at the particles generation chamber 101 together with the carrier gas supplied at the constant mass flow rate of Qa are carried into a charge chamber 301, at which chamber the particles are charged univalent by the α rays of the radioactive isotope americium (Am).

The high-purity particles charged univalent in the charge chamber 301 flow into the differential mobility analyzer 303 through the particles inflow pipe 302, which pipe is equidistantly separated into four divisions, which divisions are disposed with 90 degrees apart from each other. The high-purity particles flowed into the differential mobility analyzer 303 of double cylindrical structure are classified into the sole diameter as required, e.g. 3.0 nm by the electrostatic field between the double cylinders, which field is formed by the direct current power source 306 charged with the voltage of e.g. −21.5 V.

Controlling the mass inflow rate of the carrier and sheath gases to be introduced as mentioned above and the mass outflow rate thereof such that those rates become equal permits the classification precision of the differential mobility analyzer 303 to approach to a theoretical value.

Figure 6:
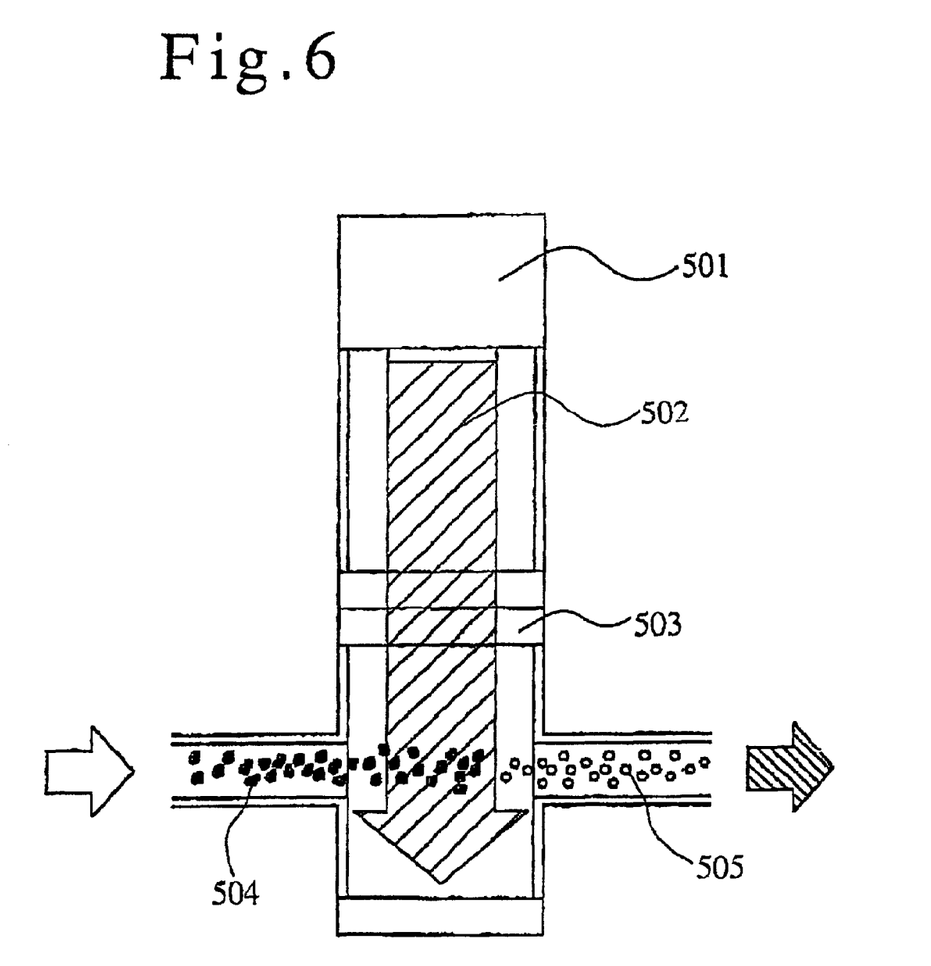
FIG. 6 is a sectional view of a standard particles heating section of the apparatus to show one example of the preferred embodiment of the present invention.

Because the high-purity standard particle of a comparatively large diameter, e.g. of 20 nm happen to be a cohesion mass 504 of the particles of smaller diameter, e.g. of 5 nm or below so that it is not necessarily of spherical uniform structure, it can be reshaped into a spherical particle 505 by irradiating to it infrared rays 502 radiated from a source 501 at a standard particles heating section 103 as shown in FIG. 6 through a synthetic quartz window 503 so as to subject it to heating treatment under the temperature of 1000 degrees Centigrade or above.

Then, the high-purity standard particles as classified in the differential mobility analyzer 303 together with the carrier gas are carried through the nozzle 402 into the particles collecting chamber 104 and emitted from the orifice 401 so as to be collected onto the substrate 404.

Here, the high-purity standard particles as classified and charged univalent immediately before being collected onto the substrate are collected at the fine current measuring terminal 409 and the transfer of electrons carried out upon the collection thereof is measured as an electric current by the ammeter 410, which allows the amount of the collected high-purity particles per unit time, e.g. circa $8 \times 10^4$ particles/$cm^3$ at 20 pA to be confirmed, which in turn controlling the collecting time thereof permits the number of the collected particles to be estimated.

Again, the alteration of the aperture in diameter of the orifice 401 to 2 mm so as to enlarge the difference between the internal pressure Pn of the nozzle 402 and that P2 of the collecting chamber where Pn amounts to 7.4 Torr while P2 amounts to 0.1 Torr allows the emitting speed of the carrier gas to the collecting chamber to increase as well as the mobility of the particles at the downstream of the nozzle to increase according to the lowering of the pressure P2, which improves the efficiency of collecting the standard particles onto the substrate by virtue of inertial force inherent in themselves.

In addition, the application of a bias voltage, e.g. 100 V onto the substrate 404 by means of the direct current power source 407 and the refrigeration, e.g. at −100 degrees Centigrade of the substrate, 404 with the introduction of liquefied nitrogen into a chamber 408 allow the efficiency of collecting the standard particles to further improve.

As described above, nanometer-sized high-purity standard particles of wide selectivity in material and monodispersive uniform structure are efficiently produced with the abatement of contamination and damage thereon by means of the high-purity standard particles production apparatus according to the present invention, which apparatus comprises a particles generation chamber to generate high-purity particles by laser ablation in an ambient gas, a particles classification chamber to classify high-purity standard particles of a diameter as required from the high-purity particles as generated in the generation chamber and a particles collecting chamber to collect the high-purity standard particles as classified.

The present invention is disclosed with the above preferred embodiment as shown in the accompanying drawings, but it should be appreciated that it can be modified or altered into various manners within the scope and spirits of the accompanying

What is claimed is:

1. High-purity standard particle production apparatus comprising a particle generation chamber to generate high-purity particles by laser ablation in an ambient gas,
   a particle classification chamber to classify high-purity standard particles of a diameter as required from said high-purity particles as generated at said particle generation chamber,
   a particle collecting chamber to collect said high-purity standard particles as classified at said classification chamber; and
   a particle heating means positioned between said particle classification chamber and said particle collecting chamber;
   wherein said particle heating means is adapted to heat the high-purity standard particles classified at said particle classification chamber by infrared radiation at a downstream position from said particle classification chamber, so that high-purity standard particles of a comparatively large diameter which are non-spherical and are composed of a cohesive mass of particles having a smaller diameter than the cohesive mass is reshaped into high-purity standard particles, and whereby the crystallization of the high-purity standard particles is improved.

2. The high-purity standard particle production apparatus according to claim 1 wherein a gas refining means is provided to substantially remove impurities contained in a raw material gas supplied as said ambient gas.

3. The high-purity standard particle production apparatus according to claim 1 wherein an orifice is provided in said particle collecting chamber to reduce a piping cross section through a passage course of said high-purity standard particles.

4. The high-purity standard particle production apparatus according to claim 1, comprising
   a particle inflow pipe means connected between the particle generation chamber and the particle classification chamber for inducing a flow of the high-purity standard particles generated at said particle generation chamber to said particle classification chamber;
   wherein the particle inflow pipe means has an equidistantly separated construction.

5. The high-purity standard particle production apparatus according to claim 4, wherein the particle classification chamber has a double cylindrical structure, the particle inflow pipe means extends from the particle generation chamber towards the particle classification chamber, and is equidistantly separated by 90 degree angles into four divisions, and the particles are charged in a univalent flow into the particle classification chamber though the particle inflow piper means which is equidistantly separated at 90 degree angles into four divisions, and the particles are supplied equally into the particle classification chamber such that the flow of particles is separated into four divisions.

6. The high-purity standard particle production apparatus according to claim 5 wherein a plurality of particle classification means are disposed in said particle classification chamber.

7. A method of producing high-purity standard particles in an apparatus connecting a particle generation chamber to generate high-purity particles, a particle classification chamber to classify the high-purity particles generated at the particle generation chamber; and a particle collecting chamber to collect said high-purity standard particles as classified at said particle classification chamber in that order, comprising:
   introducing a carrier gas of a low concentration of impurities into the particle generation chamber;
   introducing a sheath gas into the particle classification chamber;
   performing differential exhaustion of a gas exhaustion system of the particle collecting chamber and exhaustion of the gas exhaustion system of the particle classification chamber by controlling the exhausting actions such that the inside of the high-purity particle generation chamber is kept to a constant pressure;
   introducing a pulse laser beam into the particle generation chamber and radiating the pulse laser beam to a target, and thus obtaining the high-purity particles;
   introducing the high-purity particles into the particle classification chamber and classifying the particles into a substantially sole predetermined diameter to obtain the high-purity standard particles;
   introducing the high-purity standard particles as classified in the particle classification chamber into the particles collecting chamber and collecting the high-purity standard particles;
   wherein said classifying in the particle classification chamber is performed under conditions wherein the mass inflow rate of the carrier gas and sheath gas to be introduced into the particle classification chamber and mass outflow rate thereof are controlled such that those rates become equal.

8. The method of producing high-purity standard particles according to claim 7, further comprising electrically charging the high-purity particles generated at the particles generation chamber, and further classifying the charged high-purity particles by a differential electric mobility analyzer.

9. The method of producing high-purity standard particles according to claim 7, wherein the action of introducing carrier gas of a low concentration of impurities into the particles generation chamber and the action of differential exhaustion of gas exhaustion system of the particle collecting chamber are parallelly performed in the radiation of the pulse laser beam to a target.

10. The method of producing high-purity standard particles according to claim 7, wherein in the collecting of the high-purity standard particles, the high-purity standard particles are carried through a nozzle into the particles collecting chamber, and collected by utilizing a difference between internal and outside pressures of the nozzle to improve the efficiency of collecting the high-purity standard particles into a substrate by virtue of inertial force inherent in the high-purity standard particles.

11. The method of producing high-purity standard particles according to claim 10, wherein in the process of collecting the high-purity standard particles, a bias voltage is applied onto the substrate.

12. The method of producing high-purity standard particles according to claim 11, wherein in the process of collecting the high-purity standard particles, the substrate onto which a bias voltage is applied is refrigerated.

* * * * *